United States Patent
Saxena et al.

(10) Patent No.: US 8,663,964 B2
(45) Date of Patent: Mar. 4, 2014

(54) METHODS OF TREATING HUMAN PAPILLOMAVIRUS

(75) Inventors: Shailendra K. Saxena, Monroe Township, NJ (US); Wojciech Ardelt, New City, NY (US)

(73) Assignee: Tamir Biotechnology, Inc., San Diego, CA (US)

( * ) Notice: Subject to any disclaimer, the term of this patent is extended or adjusted under 35 U.S.C. 154(b) by 33 days.

(21) Appl. No.: 13/186,501

(22) Filed: Jul. 20, 2011

(65) Prior Publication Data

US 2013/0022589 A1 Jan. 24, 2013

(51) Int. Cl.
- *C12N 9/22* (2006.01)
- *C12N 9/00* (2006.01)
- *A61K 38/43* (2006.01)
- *A61K 38/46* (2006.01)

(52) U.S. Cl.
USPC .......... 435/199; 435/183; 424/94.1; 424/94.6

(58) Field of Classification Search
None
See application file for complete search history.

(56) References Cited

U.S. PATENT DOCUMENTS 7,572,882 B2 * 8/2009 Sette et al. .................... 530/300
2009/0246214 A1 * 10/2009 Goldenberg et al. ...... 424/184.1

OTHER PUBLICATIONS

Durmazlar et al., J. Dermatol. Treatment 20(2): 114-119 (2009).*
Hariri et al., Centers for Disease Control VPD Surveillance Manual, 5th edition, Chapter 5, pp. 1-11 (2011).*
Trimble et al., Lancet Oncol. 10: 975-980 (2009).*

* cited by examiner

*Primary Examiner* — Patricia A Leith
*Assistant Examiner* — Erin M Bowers
(74) *Attorney, Agent, or Firm* — Mark H. Jay

(57) ABSTRACT

Two RNases (ranpirnase and the second embodiment disclosed in U.S. Pat. No. 5,728,805) are tested against human papillomavirus infections. QRT-PCR assays indicate that the RNases have anti-viral activity against type 11 HPV.

5 Claims, 1 Drawing Sheet

Activity of Ranpirnase,
Ranpirnase Variant ("'805 variant", $Val_{11}$, $Asn_{20}$, $Arg_{103}$ – Ranpirnase),
and Cidofovir
Against Human Papillomavirus Infections

| Compound | $EC_{50}$ (µM) | $CC_{50}$ (µM) | SI |
|---|---|---|---|
| Ranpirnase | 0.051 | 6.77 | 133 |
| Ranpirnase Variant | 0.025 | 5.9 | 236 |
| Cidofovir (control) | 125.4 | 716.3 | 5.7 |

Activity of Ranpirnase,
Ranpirnase Variant ("'805 variant", $Val_{11}$, $Asn_{20}$, $Arg_{103}$ – Ranpirnase),
and Cidofovir
Against Human Papillomavirus Infections

| Compound | $EC_{50}$ (µM) | $CC_{50}$ (µM) | SI |
|---|---|---|---|
| Ranpirnase | 0.051 | 6.77 | 133 |
| Ranpirnase Variant | 0.025 | 5.9 | 236 |
| Cidofovir (control) | 125.4 | 716.3 | 5.7 |

METHODS OF TREATING HUMAN PAPILLOMAVIRUS

BACKGROUND OF THE INVENTION

The invention relates to virus infections, and more particularly relates to treatment of human papillomavirus ("HPV") in living subjects. In its most immediate sense, the invention relates to treatment of type 11 human papillomavirus using certain ribonucleases (RNases), namely ranpirnase (known also by its registered trademark ONCONASE) and the '805 variant of ranpirnase described below.

Ranpirnase is an RNase. It is disclosed and claimed in U.S. Pat. No. 5,559,212. It has been tested and found to be cytotoxic to cancer cells because of its enzymatic activity against RNA. The second embodiment disclosed and claimed in U.S. Pat. No. 5,728,805 (hereinafter, the "'805 variant") is also an RNase, and has likewise been found to be cytotoxic to certain cancer cells. The '805 variant is a close variant of ranpirnase; its amino acid sequence is identical to that of ranpirnase except that it has valine instead of isoleucine at position 11, asparagine instead of aspartic acid at position 20, and arginine instead of serine at position 103. (In the drawings, the '805 variant is referred to as "$Val_{11}, Asn_{20}, Arg_{103}$—Ranpirnase".)

Presently, there is no satisfactory treatment for HPV infections. While vaccines (e.g. those available under the GARDASIL and CERVARIX trademarks) can prevent infection with HPV, for patients who are infected with HPV existing treatments (cellular immune inducers and anti-mitotic agents) are ineffective. This is of concern because HPV infections can develop into cervical cancer.

Ranpirnase and the referenced '805 variant have been discovered to be surprisingly active against certain HPV infections. Ranpirnase is known to be non-toxic and well-tolerated in humans, and the other RNase is believed to share these qualities. In accordance with the invention, HPV infections, and particularly type 11 HPV infections, are treated using these RNases by administering them in therapeutically effective amounts.

BRIEF DESCRIPTION OF THE DRAWING

In the drawing, wherein $EC_{50}$ is the concentration (expressed in μM) of the test RNase that inhibited virus replication by 50%, $CC_{50}$ is the tested compound dose (expressed in μM) at which 50% of total cellular RNA was recovered, SI, the selective index, is $CC_{50}/EC_{50}$. The higher the value of SI, the more active is the tested RNase, Control $EC_{50}$ is the concentration (expressed in μM) of a control drug that inhibited virus replication by 50%. The control drug is cidofovir:

FIG. 1 shows the results of testing the anti-viral activity of ranpirnase and the '805 variant against type 11 HPV.

DETAILED DESCRIPTION OF PREFERRED EMBODIMENTS

To evaluate the activity of the tested RNases against type 11 HPV infections, the following quantitative PCR assay was used:

Solutions of the tested RNases were prepared in cell culture medium without use of dimethyl sulfoxide ("DMSO"). DMSO is unnecessary because the tested RNases are water-soluble.

HPV is an DNA virus. Antiviral activity against HPV type 11 was evaluated using a quantitative reverse transcriptase PCR (QRT-PCR) assay. Initially, on Day 1, 1 million A-431 cells were placed in 6-well dishes in Dulbecco's Modified Eagle Medium ("DMEM") supplemented with 10% fetal bovine serum ("FBS"). The cells were then incubated for two days at 37° C.

After this incubation period, on day 2 replicate aliquots of HPV-11 were added to each non-control well, representing a multiplicity of infection ("MOI") of 150 particles per cell in DMEM containing 2.5% FBS. Control wells did not receive HPV-11.

One day later, i.e. on day 3, DMEM with 10% FBS was added to each cell culture well.

One day later, i.e. on day 4, the tested compounds were added to the non-control cell culture wells. Control wells received media alone, or the vehicle used to dilute the tested compounds. Cidofovir diluted to 300 ug/ml was used as a positive control.

72 hours later, on day 7, the cell cultures were harvested and then lysed with Trizol reagent (purchased from Gibco/BRL), and RNA is prepared.

Finally, one day later, on day 8, QRT-PCR was carried out to quantitate the proportion of viral E1^E4 transcripts and a cellular reference RNA for the TATA-binding protein ("TBP"). The anti-viral effect of each tested compound was assessed as an EC50 value at which the amount of E1^E4 viral transcript was reduced by 50% when compared with cultures infected only with HPV-11.

Evaluation Results

The National Institute of Allergy and Infectious Diseases (NIAID) (a component of the National Institute of Health) uses a Selectivity Index (SI) ratio as a common indicator to assess the potency of a test compound. SI, which equals CC50/EC50, measures the ability of the tested RNase to inhibit replication of a viral infection without killing the infected cells. Where SI in the accompanying Figure is greater than 1, the RNase under test is active against the virus indicated, and increasing values of SI indicate increasing activity.

Thus, as can be seen in FIG. 1, ranpirnase and the '805 variant are each extraordinarily active against type 11 HPV. More particularly, when the $EC_{50}$ value for the positive control drug cidofovir is compared with the $EC_{50}$ value of ranpirnase, it can be seen that ranpirnase requires one two thousand four hundred fifty ninth (1/2459) of the quantity of cidofovir needed to inhibit replication of the HPV virus by 50%. Similarly, reduction HPV replication by 50% using the '805 variant requires only one five thousand sixteenth (1/5016) of the quantity of cidofovir needed to bring about the same reduction of virus replication.

This is a most unusual result; as stated above, existing therapies for HPV are cellular immune inducers and anti-mitotic agents and these do not act against HPV directly.

Because SI measures the ability of a substance under test to inhibit replication of a particular virus without killing the infected cells themselves, it is reasonably correlated with usefulness of the substance in treating a living subject that is infected with the virus. Accordingly, test results in which SI>1 indicate that living subjects infected with HPV, and particularly type 11 HPV, can be treated by administration of an appropriate dose of the corresponding RNase.

Although at least one preferred embodiment of the invention has been described above, this description is not limiting and is only exemplary. The scope of the invention is defined only by the claims, which follow:

The invention claimed is:

1. A method of treating human papillomavirus (HPV), comprising the step of directly applying a therapeutically effective amount of ranpirnase to an HPV-infected region of a living subject in need of such treatment.

2. A method of treating human papillomavirus, comprising the step of directly applying a therapeutically effective amount of a polypeptide having the amino acid sequence of SEQ ID NO.: 1 to an HPV-infected region of a living subject in need of such treatment.

3. A method of treating type 11 human papillomavirus (HPV), comprising the step of directly applying a therapeutically effective amount of ranpirnase to an HPV-infected region of a living subject in need of such treatment.

4. A method of treating type 11 human papillomavirus, comprising the step of directly applying a therapeutically effective amount of a polypeptide having the amino acid sequence of SEQ ID NO.: 1 to an HPV-infected region of a living subject in need of such treatment.

5. A method of treating human papillomavirus (HPV), comprising the step of directly applying a therapeutically effective amount of:
 a. ranpirnase, or
 b. a polypeptide having the amino acid sequence of SEQ ID NO.: 1 to an HPV-infected region of a living subject in need of such treatment.

* * * * *

SEQUENCE LISTING

```
<160> NUMBER OF SEQ ID NOS: 1

<210> SEQ ID NO 1
<211> LENGTH: 104
<212> TYPE: PRT
<213> ORGANISM: Rana pipiens
<220> FEATURE:
<221> NAME/KEY: MOD_RES
<222> LOCATION: (1)..(1)
<223> OTHER INFORMATION: BLOCKED
<300> PUBLICATION INFORMATION:
<310> PATENT DOCUMENT NUMBER: 5728805
<312> PUBLICATION DATE: 1998-03-17

<400> SEQUENCE: 1

Glu Asp Trp Leu Thr Phe Gln Lys Lys His Val Thr Asn Thr Arg Asp
1               5                   10                  15

Val Asp Cys Asn Asn Ile Met Ser Thr Asn Leu Phe His Cys Lys Asp
            20                  25                  30

Lys Asn Thr Phe Ile Tyr Ser Arg Pro Glu Pro Val Lys Ala Ile Cys
        35                  40                  45

Lys Gly Ile Ile Ala Ser Lys Asn Val Leu Thr Thr Ser Glu Phe Tyr
    50                  55                  60

Leu Ser Asp Cys Asn Val Thr Ser Arg Pro Cys Lys Tyr Lys Leu Lys
65                  70                  75                  80

Lys Ser Thr Asn Lys Phe Cys Val Thr Cys Glu Asn Gln Ala Pro Val
                85                  90                  95

His Phe Val Gly Val Gly Arg Cys
            100
```